US00PP11348P

United States Patent [19]

McSpadden, Jr.

[11] Patent Number: Plant 11,348

[45] Date of Patent: Apr. 11, 2000

[54] APPLE TREE NAMED 'CAITLIN'

[75] Inventor: Charles L. McSpadden, Jr., Cleveland, Tenn.

[73] Assignee: Stark Bro's Wholesale Co., Louisiana, Mo.

[21] Appl. No.: 09/004,304

[22] Filed: Jan. 8, 1998

[51] Int. Cl.[7] ..... A01H 5/00

[52] U.S. Cl. ..... Plt./162

[58] Field of Search ..... Plt./161, 162, 172

[56] References Cited

U.S. PATENT DOCUMENTS

P.P. 4,121 10/1977 Ten Hove ..... Plt./162

*Primary Examiner*—Howard J. Locker
*Assistant Examiner*—Wendy A Baker
*Attorney, Agent, or Firm*—Burns, Doane, Swecker & Mathis, L.L.P.

[57] ABSTRACT

A new and distinct cultivar of Gala-type apple tree is provided which originated as a partial tree mutation of the 'Tenroy' cultivar (U.S. Plant Pat. No. 4,121) growing at Cleveland, Tenn. The new cultivar forms considerably larger fruit that ripens earlier than that of the 'Tenroy' cultivar. It also blooms earlier than the 'Tenroy' cultivar. The five swollen areas or bumps at the calyx end of the fruit tend to be more pronounced than those of the 'Tenroy' cultivar. The tips of the current year's growth tend to be thicker than those of the 'Tenroy' cultivar. The leaves tend to be generally smaller and more rigid than those of the 'Tenroy' cultivar. Also, the leaf stems tend to be shorter than those of the 'Tenroy' cultivar. The fruit is flavorfully mild and of good quality similar to that of the 'Tenroy' cultivar.

4 Drawing Sheets

SUMMARY OF THE INVENTION

The new cultivar originated as a partial tree mutation (i.e., upper tree mutation) of the 'Tenroy' cultivar (U.S. Plant Pat. No. 4,121). The 'Tenroy' cultivar is known to be a mutation of the 'Kidd's D-8' cultivar (U.S. Plant Pat. No. 3,637). The mutation of the present invention was discovered among trees of the 'Tenroy' cultivar budded on Malling Merton 111 rootstock. Such 'Tenroy' trees had been obtained under the ROYAL GALA trademark from Stark Brothers Nurseries and Orchards Company of Louisiana, Miss., and were planted during 1989. More specifically, it was discovered during 1995 that all branches from a single tree starting about 30 inches above ground level formed distinctive fruit with an earlier ripening date. It was observed that the lower branches of the original tree continued to exhibit the expected characteristics of the 'Tenroy' cultivar as did all other 'Tenroy' trees growing in the same area. The new cultivar has been preserved and has been carefully studied.

It has been confirmed that the new cultivar possesses a novel combination of characteristics and constitutes a commercially important addition to the previously available cultivars of Gala-type apple trees. Had the new cultivar of the present invention not been discovered and preserved it would have been lost to mankind.

It has been found that the new Gala-type apple tree of the present invention exhibits the following combination of characteristics:

(a) forms larger fruit than the 'Tenroy' cultivar (U.S. Plant Pat. No. 4,121),
(b) forms fruit wherein the five swollen areas at the calyx end of the fruit tend to be more pronounced than those of the 'Tenroy' cultivar,
(c) forms blooms earlier and forms fruit that ripens earlier than that of the 'Tenroy' cultivar,
(d) forms current-year growth tips that are thicker than those of the 'Tenroy' cultivar,
(e) forms generally smaller leaves than the 'Tenroy' cultivar that tend to be thicker and more rigid, and
(f) forms leaf stems that tend to be shorter than those of the 'Tenroy' cultivar, Asexual propagation by budding conducted at Louisiana, Miss., has demonstrated that the unique combination of characteristics of the new cultivar comes true to form and is established and reliably transmitted through succeeding generations.

BRIEF DESCRIPTION OF THE PHOTOGRAPHS

The accompanying photographs show typical specimens of the new cultivar as depicted in color as nearly true as it is reasonably possible to make the same in color illustrations of this character.

FIG. 1 illustrates typical blossoms of the new cultivar as formed on immature trees in a test planting located at Wapato, Wash.

FIG. 2 illustrates a typical mature fruit of the new cultivar at the center. For comparative purposes, a typical fruit of the parent 'Tenroy' cultivar (U.S. Plant Pat. No. 4,121) is shown at the right and a typical fruit of the 'Obrogala' cultivar (U.S. Plant Pat. No. 8,621) is shown at the left. The larger fruit size of the new cultivar is apparent. The illustrated fruits were produced in a test planting located at Wapato, Wash., wherein trees of the new cultivar were immature.

FIG. 3 illustrates for comparative purposes typical one year-old tip shoots of the new cultivar at the top and of the parent 'Tenroy' cultivar at the bottom. The trees that produced the tip shoots were grown at Cleveland, Tenn. It will be noted that current year's growth tips (i.e., at least the last 30 cm.) of the new cultivar generally are thicker as are the tip buds of the new cultivar.

Figure 6:
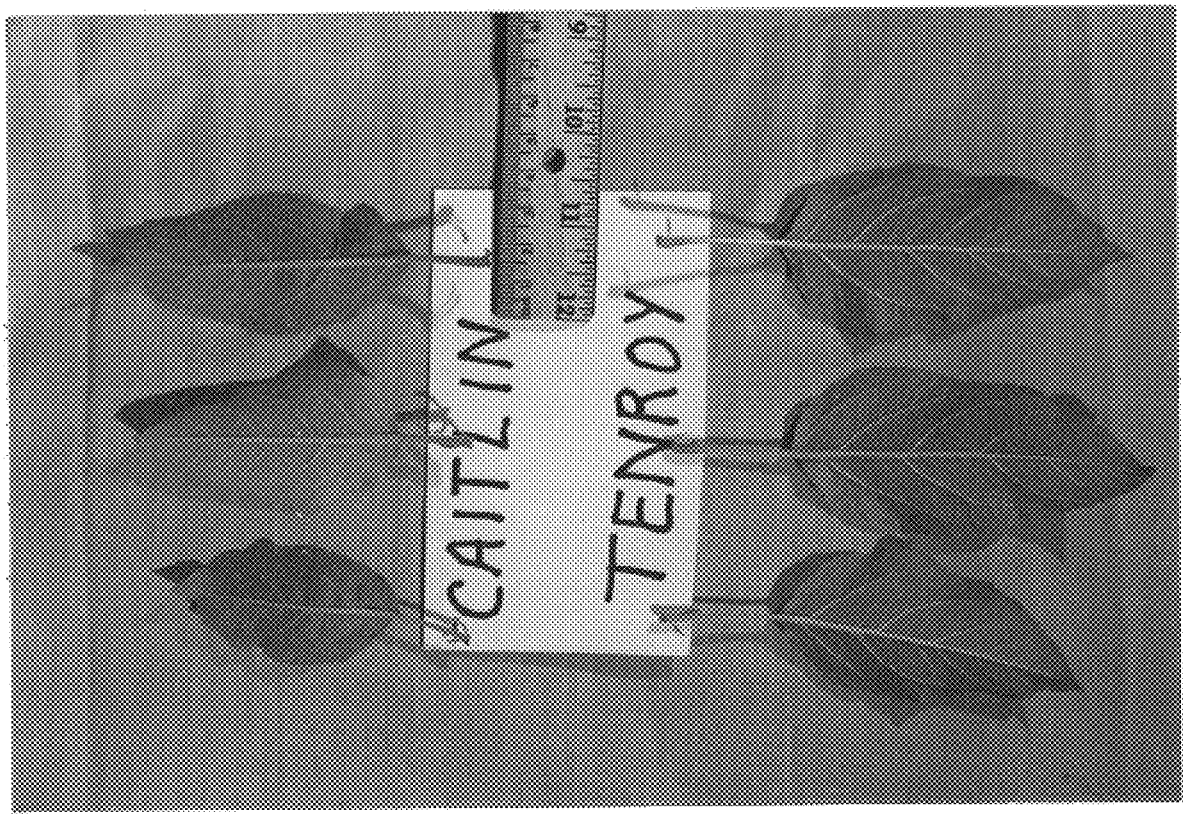

FIG. 6 illustrates for comparative purposes the under surfaces of typical leaves of the new cultivar at the left and of the parent 'Tenroy' cultivar at the right. The generally smaller leaf size of the new cultivar is apparent. The trees that produced the illustrated leaves were grown at Cleveland, Tenn.

Figure 7:
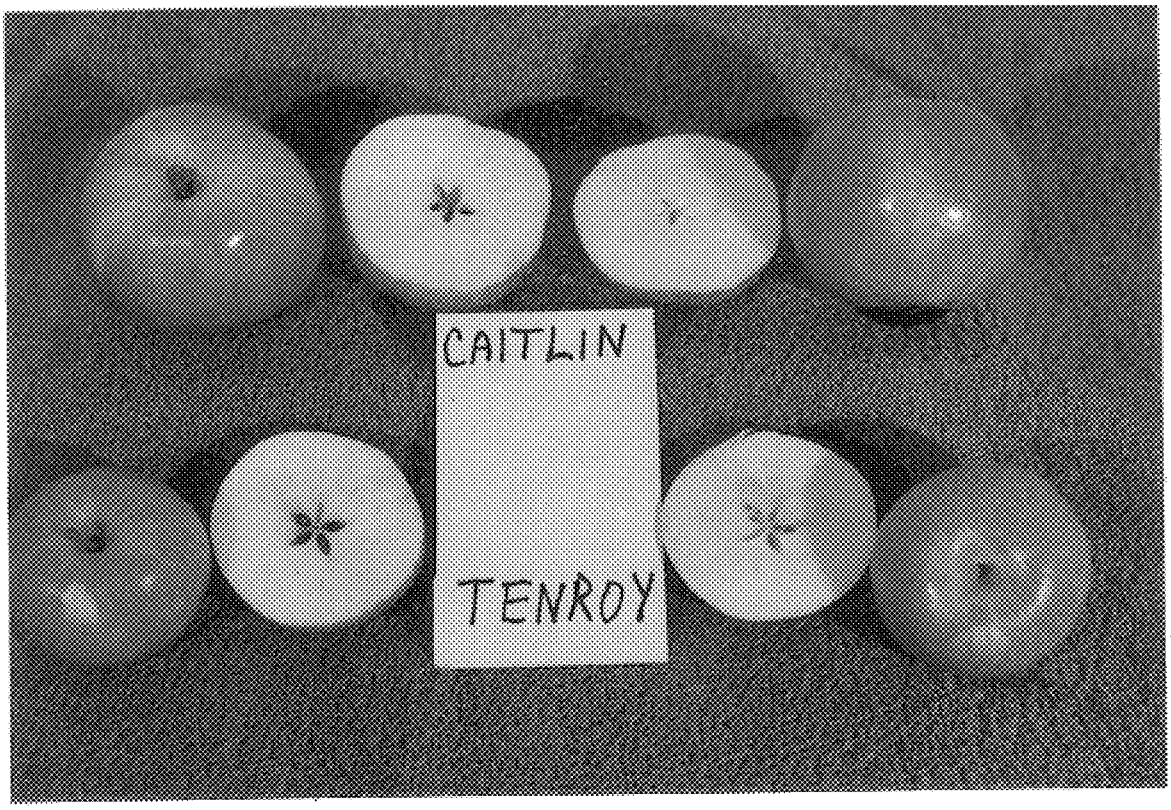

FIG. 7 illustrates for comparative purposes typical mature fruit of the new cultivar at the top and of the parent 'Tenroy' cultivar at the bottom. The trees that produced the illustrated fruit were grown at Cleveland, Tenn.

Figure 8:
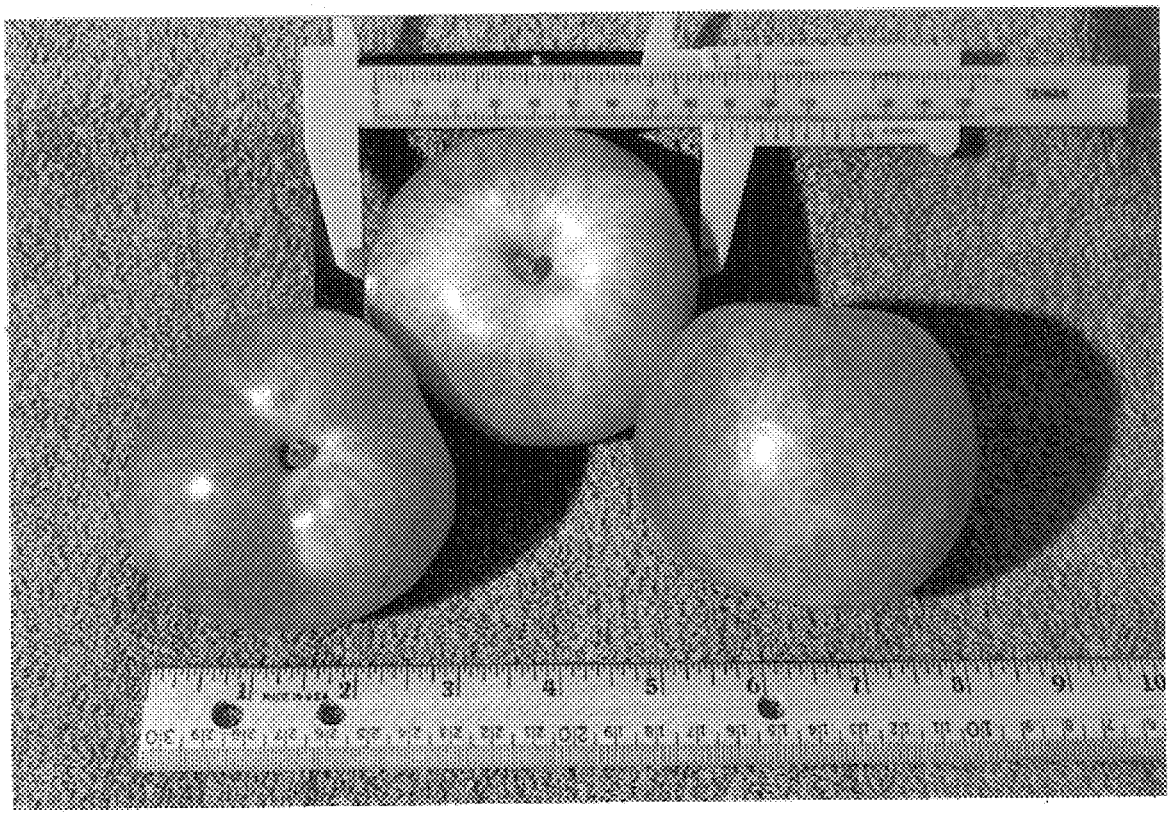

FIG. 8 illustrates a closer view of three typical mature apples of the new cultivar wherein the large size and the typical fruit coloration are apparent. The trees that produced the fruit were grown at Cleveland, Tenn.

DETAILED DESCRIPTION

The following is a detailed description of the new cultivar (*Malus domestica* 'Caitlin') when grown at Cleveland, Tenn. Since the inherent characteristics of the new cultivar may be influenced somewhat by the environment, in some instances observations of immature trees obtained at Wapato, Wash., also are included. Color information is provided by reference to The R.H.S. Colour Chart of The Royal Horticultural Society, London.

Tree: Medium size, vigorous, spreading, round-topped, hardy, very productive and regular bearing. A typical five year-old tree of the new cultivar on 'Malling Merton 26' rootstock has an average height of approximately 10.5 feet and an average breadth of approximately 7.5 feet.

*Trunk.*—Medium and smooth.

Figure 3:
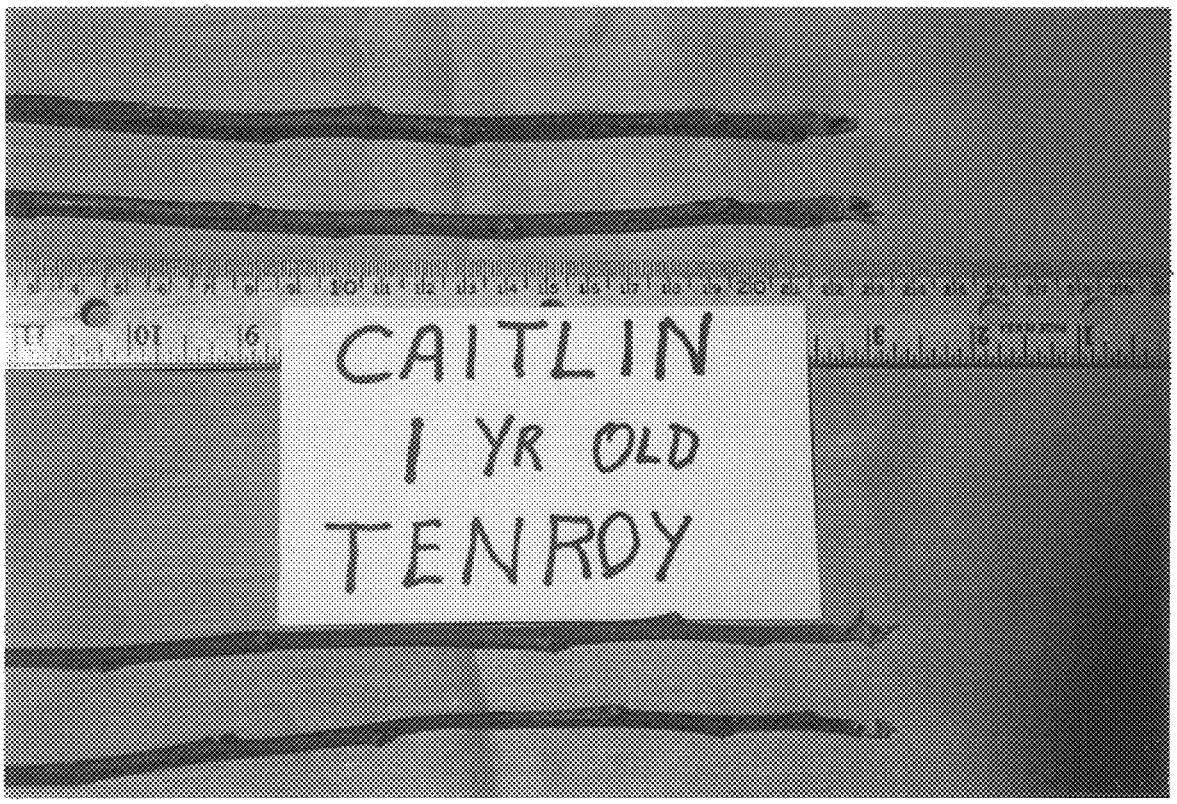
Figure 4:
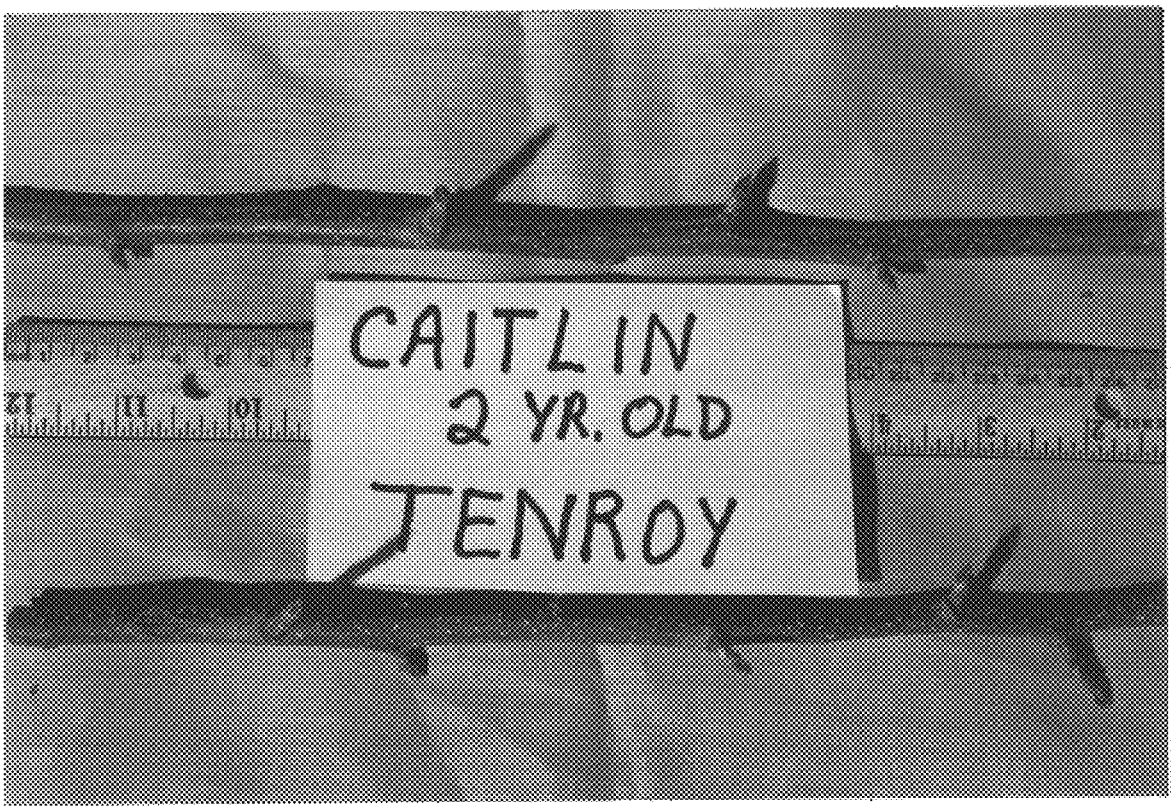
FIG. 4 illustrates for comparative purposes typical two year-old twigs of the new cultivar at the top and of the parent 'Tenroy' cultivar at the bottom. The trees that produced the twigs were grown at Cleveland, Tenn.
Figure 5:
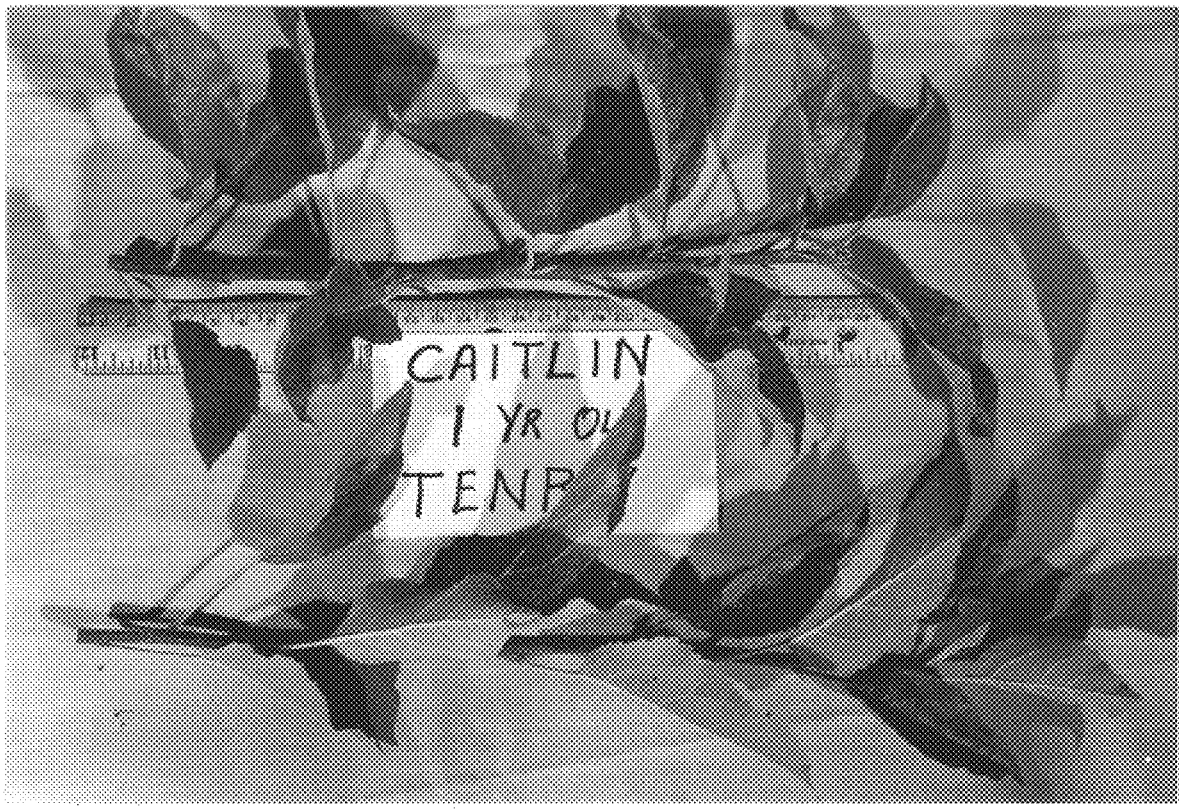
FIG. 5 illustrates for comparative purposes one year-old branches with foliage (upper and under surfaces) of the new cultivar at the top and of the parent 'Tenroy' cultivar at the bottom. The trees that produced the branches were grown at Cleveland, Tenn.

*Branches.*—Medium thick, smooth, much branching, some intermittent swelling tends to form at the bases of branches, new limb growth tends to be more stubby and less tapered than that of the 'Tenroy' cultivar (as illustrated in FIG. 3), and the coloration is near Brown Group 200C. The average new growth on a five year-old tree in approximately 2.5 to 3 feet per year.

*Lenticels.*—Numerous and medium large in size.

*Leaf form.*—Medium thick, the leaves tend to be somewhat thicker than those of the 'Tenroy' cultivar, and the leaves are abruptly pointed. The center vein and major side veins are generally thicker than those of the 'Tenroy' cultivar thereby making the leaves somewhat more rigid.

*Leaf color.*—Green Group 137A on the upper surface and lighter green on the under surface (as illustrated).

*Leaf margins.*—Crenate, finely serrate. Such serration tends to be slightly finer than that of the 'Tenroy' cultivar.

*Leaf size.*—When typical leaves were measured on Jul. 30, 1997, the average length was approximately 7.9 cm. and the average width was approximately 4.5 cm. to yield width to length ratio of approximately 0.6:1. This compares to an average length of approximately 8.5 cm. and an average width of 4.4 cm. and a width to length ratio of approximately 0.5:1 for the 'Tenroy' cultivar growing nearby.

*Petioles.*—When measured on Jul. 30, 1997, the average length was approximately 2.4 cm. This compares to an average length of approximately 3.1 cm. for the 'Tenroy' cultivar growing nearby.

Figure 1:
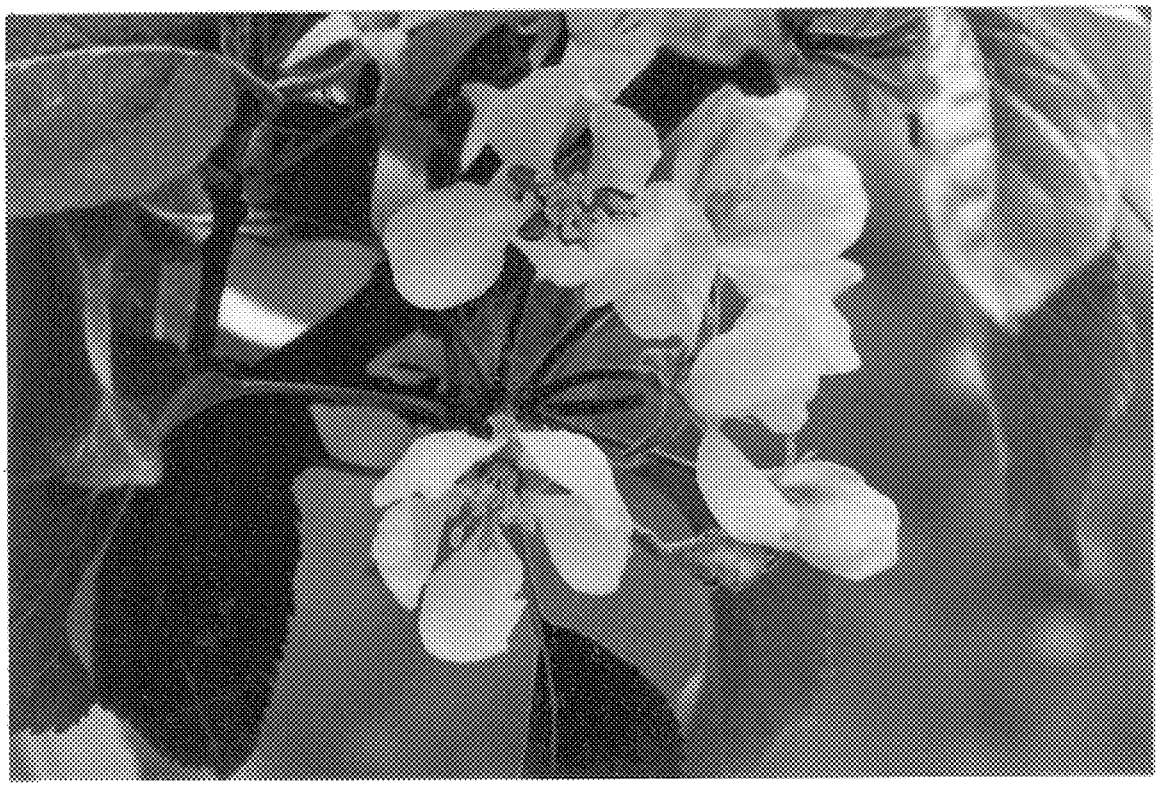
Figure 2:
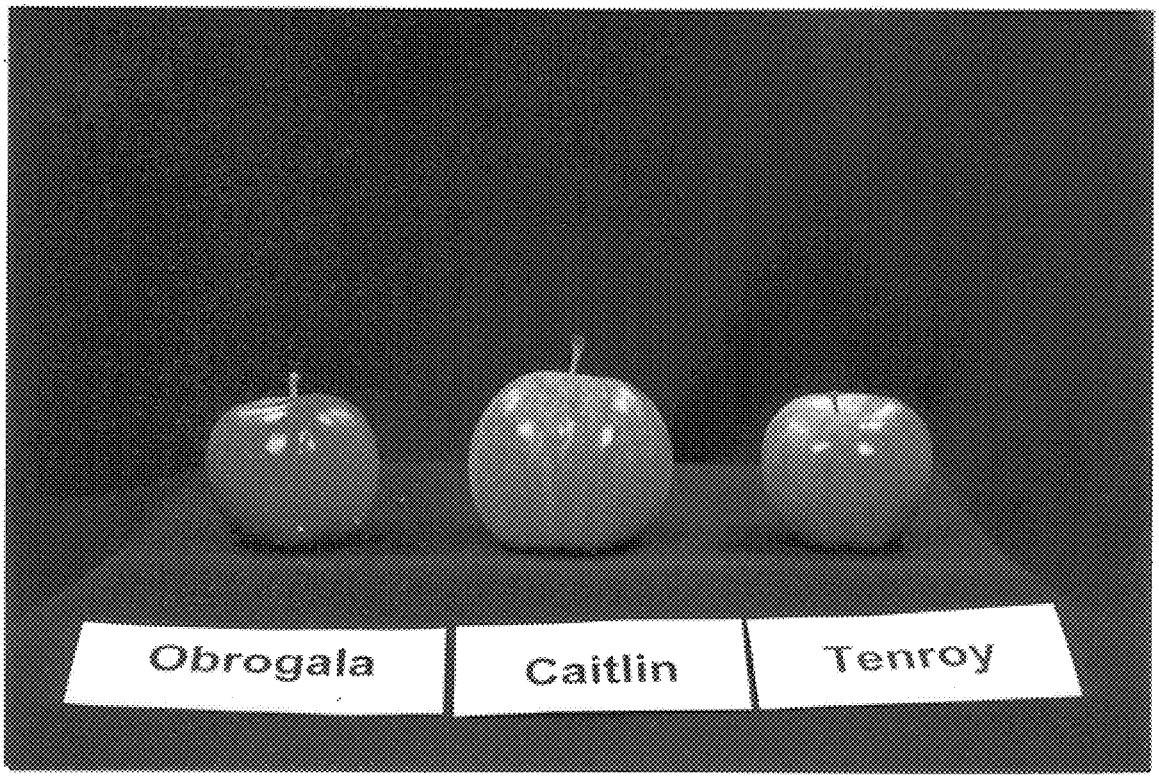

Flowers: Peak blooms appear approximately 3 to 5 days prior to those of the 'Tenroy' cultivar. The coloration is white with pink fading to white (i.e., near White Group 155A) on the reverse side. The flower characteristics, including the flower size, appear to be substantially identical to those of the 'Tenroy' cultivar. See FIG. 1. The new variety is a diploid. An early to mid-season bloomer is required for pollination. Preferred pollinators are the 'Empire' and 'Red Delicious' cultivars. Cultivars such as 'Rome Beauty' and 'York' are not suitable pollinators because of their late bloom dates.

Fruit:

*Ripening date.*—Ripening occurs approximately August $6^{th}$ (e.g., August $1^{st}$ to $14^{th}$) at Cleveland, Tenn., which is approximately 3 to 5 days before the 'Tenroy' cultivar. Ripening occurs approximately August $10^{th}$ (e.g., August $5^{th}$ to $20^{th}$) at Wapato, Wash., which also is approximately 3 to 5 days before the 'Tenroy' cultivar.

*Size.*—When typical developing apples were measured on Jun. 20, 1997, it was found that their transverse diameters averaged approximately 6.1 cm. compared to an average transverse diameter of approximately 5 cm. for the 'Tenroy' cultivar. When typical developing apples were measured on Jul. 1, 1997, it was found that their transverse diameters averaged approximately 6.6 cm. compared to an average transverse diameter of approximately 5.5 cm. for the 'Tenroy' cultivar. When typical developing apples were measured on Jul. 21, 1997, it was found that their transverse diameters averaged approximately 7.7 cm. compared to an average transverse diameter of approximately 6.2 cm. for the 'Tenroy' cultivar. During the August, 1997, harvest, it was found that the average transverse diameters for mature apples measured approximately 8.1 cm. compared to an average transverse diameter of approximately 6.7 cm. for the 'Tenroy' cultivar. When typical developing apples were measured on Jun. 20, 1997, it was found that their heights averaged approximately 5 cm. compared to an average height of approximately 4.4 cm. for the 'Tenroy' cultivar. When typical developing apples were measured on Jul. 1, 1997, it was found that their heights averaged approximately 5.6 cm. compared to an average height of approximately 5 cm. for the 'Tenroy' cultivar. When typical developing apples were measured on Jul. 21, 1997, it was found that their heights averaged approximately 6.3 cm. compared to an average height of approximately 5.4 cm. for the 'Tenroy' cultivar. During the August 1997 harvest, it was found that average height was approximately 7.1 cm. compared to an average height of approximately 6 cm. for the 'Tenroy' cultivar. During the August 1997 harvest, six of the largest apples from the original tree of the 'Caitlin' cultivar had an average weight of 8.6 oz. and six of the largest apples harvested from adjacent trees of the 'Tenroy' cultivar had an average weight of 4.7 oz.

*Form.*—Generally the fruit is more ovate than that of the 'Tenroy' cultivar. During the initial months of fruit development, the sides of the fruit exhibit more pronounced vertical ribs. The appearance is similar to that of a peeled orange with vertical indented areas. However, at harvest time the vertical depressions tend to become filled somewhat and are not as noticeable as at an earlier stage in the development. Accordingly, a transverse section of a mature fruit will be nearly round with only slight irregularity.

Such irregularity also is exhibited by the fruit of the 'Tenroy' cultivar, but tends to be less noticeable due to the generally smaller fruit size. The fruit of the 'Tenroy' cultivar tends to be more globose. However, when the new cultivar was grown at Wapato, Wash., the fruit formed on immature trees tended to be more globose-conical and less typey than that of the 'Tenroy' and 'Obrogala' cultivars. Stem cavities having depths of approximately 12 to 17 mm. and breadths of approximately 25 to 28 mm. have been observed. Fruit basins having depths of approximately 19 to 22 mm. and breadths of approximately 30 mm. have been observed.

*Cavity.*—Symmetrical, acute, and tends to be not as deep and more obtuse than that of the 'Tenroy' cultivar.

*Basin.*—Symmetrical, abrupt undulate, commonly with five distinct bumps or swollen areas. When the new cultivar is grown at Wapato, Wash., the fruit formed on immature trees possessed basins that were somewhat wider.

*Stem.*—Slightly thicker and shorter than that of the 'Tenroy' cultivar, clubbed, stout, pubescent, commonly approximately 3 mm. in diameter and approximately 33 mm. in length, and commonly with a slight protrusion on one side that extends the length of the stem.

*Calyx.*—Closed, consisting of curved broadly lanceolate segments that are persistent, pubescent on both surfaces, erect, and are commonly separated at the base.

*Skin.*—Thin, smooth, glossy, little waxed, and with many small generally circular somewhat obscure dots. The color of the dots is pale yellow. When grown at Cleveland, Tenn., the ground color was near Yellow Group 4C, and when grown at Wapato, Wash., the ground color of fruit produced on immature trees was a more vivid Yellow Group 5C. The striping is modest as is that of the 'Tenroy' cultivar. When grown at Cleveland, Tenn. there is little bloom and moderate scarfskin which projects a whitish overcolor that is similar to that of the 'Tenroy' cultivar. No significant bloom or scarfskin has been observed to date for fruit of the new cultivar produced on immature trees at Wapato, Wash. The overcolor was near Red Group 43B when grown at Cleveland, Tenn. and a more vivid Red Group 42 to 45A when produced on immature trees at Wapato, Wash. Under such growing conditions at Wapato, Wash., the 'Tenroy' cultivar tends to exhibit a ground color of Yellow Group 5C to 6D and an overcolor of Red Group 42A to 45A. Regardless of the growing location, the fruit coloration is substantially the same as that of the 'Tenroy' cultivar.

*Flesh.*—Juicy, satiny, creamy white, firm, tender, fine, crisp, and equal to that of the 'Tenroy' cultivar. The flavor is mild delicate and rich. The keeping quality is the best.

*Core.*—Sessile. The bundle area in longitudinal section is oblate. The bundles are inconspicuous. The core lines are clasping and indistinct. The calyx tube is funnel- shaped, similar to that of the 'Tenroy' cultivar and is approximately 15 mm. in length. The stem of the funnel is similar to that of the 'Tenroy' cultivar. The depth of the tube to shoulder is approximately 9 mm. Styles are present. The stamens are median and tend to be present in one distinct whorl. The seed cells are axile, open, thin and orbicular. The cell walls are thin and proportionately the same as those of the 'Tenroy' cultivar. The longitudinal section is orbicular and obtuse at the apex.

*Seeds.*—Approximately 8 mm. in length and approximately 4.5 mm. in width. Five seeds are formed per apple with one seed per cell in observations to date. The seed coloration is substantially the same as that of the 'Tenroy' cultivar.

Use: Market, dessert.

Keeping quality: Good. The firm fruit has been stored up to six months under standard cold storage conditions. Under a controlled atmosphere even longer storage times should be possible.

Resistance to insects: Good. Similar to other Gala-type cultivars.

Resistance to diseases: Good. Similar to other Gala-type cultivars.

Productivity: The fruit is larger and the production is greater than that of the 'Tenroy' cultivar. A typical mature tree on 'Malling Merton 111' rootstock has been found to yield approximately 360 pounds of fruit per year.

I claim:

1. A new and distinct cultivar of Gala-type apple tree which exhibits the following combination of characteristics:

(a) forms larger fruit than the 'Tenroy' cultivar (U.S. Plant Pat. No. 4,121),
(b) forms fruit wherein the five swollen areas at the calyx end of the fruit tend to be more pronounced than those of the 'Tenroy' cultivar,
(c) forms blooms earlier and forms fruit that ripens earlier than that of the 'Tenroy' cultivar,
(d) forms current-year growth tips that are thicker than those of the 'Tenroy' cultivar,
(e) forms generally smaller leaves than the 'Tenroy' cultivar that tend to be thicker and more rigid, and
(f) forms leaf stems that tend to be shorter than those of the 'Tenroy' cultivar;

substantially as herein shown and described.

* * * * *